United States Patent
Kelkar et al.

(10) Patent No.: US 10,703,714 B2
(45) Date of Patent: Jul. 7, 2020

(54) PROCESS FOR THE SYNTHESIS OF AROMATIC CARBAMATES

(71) Applicant: COUNCIL OF SCIENTIFIC AND INDUSTRIAL RESEARCH, New Delhi (IN)

(72) Inventors: Ashutosh Anant Kelkar, Pune (IN); Nayana Tushar Nivangune, Pune (IN); Vilas Hari Rane, Pune (IN)

(73) Assignee: COUNCIL OF SCIENTIFIC AND INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 16/617,144

(22) PCT Filed: May 25, 2018

(86) PCT No.: PCT/IN2018/050335
§ 371 (c)(1),
(2) Date: Nov. 26, 2019

(87) PCT Pub. No.: WO2018/216036
PCT Pub. Date: Nov. 29, 2018

(65) Prior Publication Data
US 2020/0148631 A1 May 14, 2020

(30) Foreign Application Priority Data
May 26, 2017 (IN) .............................. 201711018554

(51) Int. Cl.
| | | |
|---|---|---|
| *C07C 269/04* | (2006.01) |
| *B01J 23/10* | (2006.01) |
| *B01J 37/08* | (2006.01) |
| *B01J 37/03* | (2006.01) |
| *B01J 37/02* | (2006.01) |
| *B01J 37/04* | (2006.01) |
| *C07C 263/04* | (2006.01) |
| *C07C 271/28* | (2006.01) |

(52) U.S. Cl.
CPC ............. *C07C 269/04* (2013.01); *B01J 23/10* (2013.01); *B01J 37/0236* (2013.01); *B01J 37/031* (2013.01); *B01J 37/04* (2013.01); *B01J 37/08* (2013.01); *C07C 263/04* (2013.01); *C07C 271/28* (2013.01)

(58) Field of Classification Search
CPC ... C07C 269/04; C07C 263/04; C07C 271/28; B01J 23/10; B01J 37/08; B01J 37/031; B01J 37/0236; B01J 37/04
See application file for complete search history.

(56) References Cited

U.S. PATENT DOCUMENTS

| | | |
|---|---|---|
| 4,268,683 A | 5/1981 | Gurgiolo |
| 5,698,731 A | 12/1997 | Bosetti et al. |
| 8,735,621 B2 | 5/2014 | Corma Canos et al. |
| 2008/0227999 A1 | 9/2008 | Molzahn |

FOREIGN PATENT DOCUMENTS

| | | |
|---|---|---|
| WO | WO 1998/055450 A1 | 12/1998 |
| WO | WO 2016/114670 A1 | 7/2016 |

OTHER PUBLICATIONS

International Searching Authority, International Search Report and Written Opinion for International Application No. PCT/IN2018/050335, dated Sep. 24, 2018, (13 pages), Rijswijk, The Netherlands.

*Primary Examiner* — Jafar F Parsa
(74) *Attorney, Agent, or Firm* — Alston & Bird LLP

(57) ABSTRACT

The present invention discloses a process for the synthesis of aromatic carbamates from amine with dialkyl carbonate in the presence of binary or ternary mixed metal oxide catalyst. The present invention further discloses the yield of said aromatic carbamate in the range of 60 to 99%. Further, the ratio of amine to dialkyl carbonate is in the range of 1:2 to 1:30.

10 Claims, 2 Drawing Sheets

(a)

(b)

PROCESS FOR THE SYNTHESIS OF AROMATIC CARBAMATES

CROSS REFERENCE TO RELATED APPLICATIONS

This application is a National Stage Application, filed under 35 U.S.C. § 371, of International Application No. PCT/IN2018/050335, filed May 25, 2018, which international application claims priority to Indian Application No. 201711018554, filed May 26, 2017; the contents of both of which as are hereby incorporated by reference in their entireties.

BACKGROUND

Related Field

The present invention relates to a process for the synthesis of carbamates. More particularly, the present invention relates to a process for the synthesis of aromatic carbamates from amine with dialkyl carbonate in the presence of mixed metal oxide catalyst.

Description of Related Art

Aromatic carbamates are valuable intermediates for the synthesis of various classes of chemicals such as pesticides, fungicides, herbicides, medical drugs, polyurethane foams and so on. In 2007 the global consumption of polyurethane as raw material was about 12 million metric tons/year and the average annual growth rate is about 5%. Carbamates are often used as stable form of isocyanate that can be easily transformed into isocyanates by thermal cracking as shown below (scheme 1).

Scheme 1
Isocyanate synthesis from carbamate

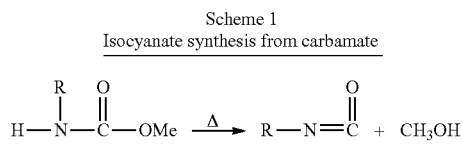

(MPC) Methyl-N-phenyl carbamate (scheme 2), (MDC) methyl-4,4'-di(phenylcarbamate) (scheme 3) and (TDC) Toluene dicarbamate (scheme 4) are safer derivatives to handle and store than corresponding isocyanates i.e MPI, MDI and TDI respectively.

Scheme 2
Synthesis of MPC from aniline and dimethyl carbonate

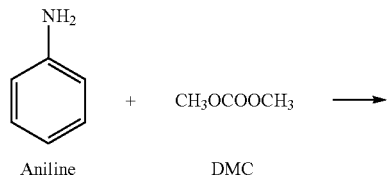

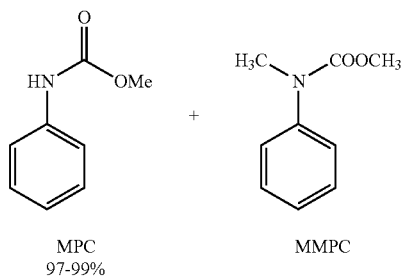

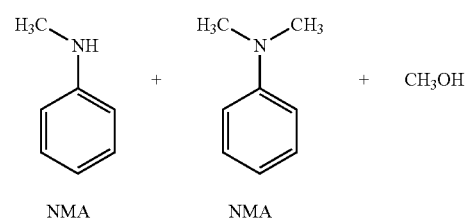

Scheme 3
Synthesis of MDC from DADPM and dimethyl carbonate

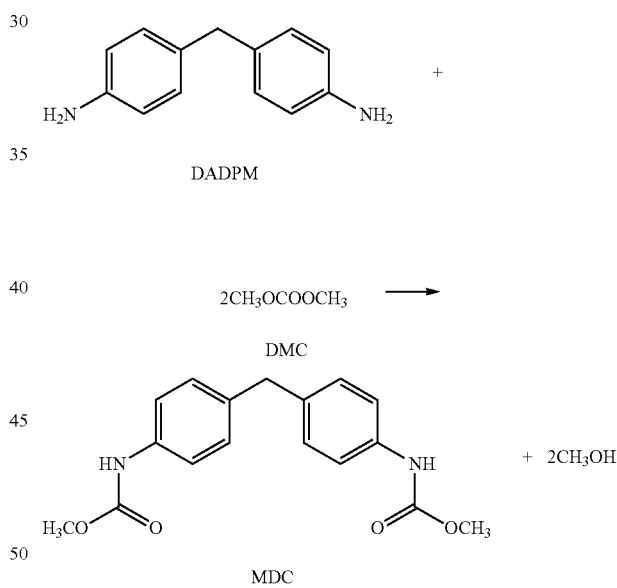

Scheme 4
Synthesis of TDC from TDA and dimethyl carbonate

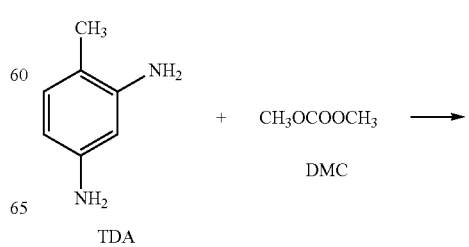

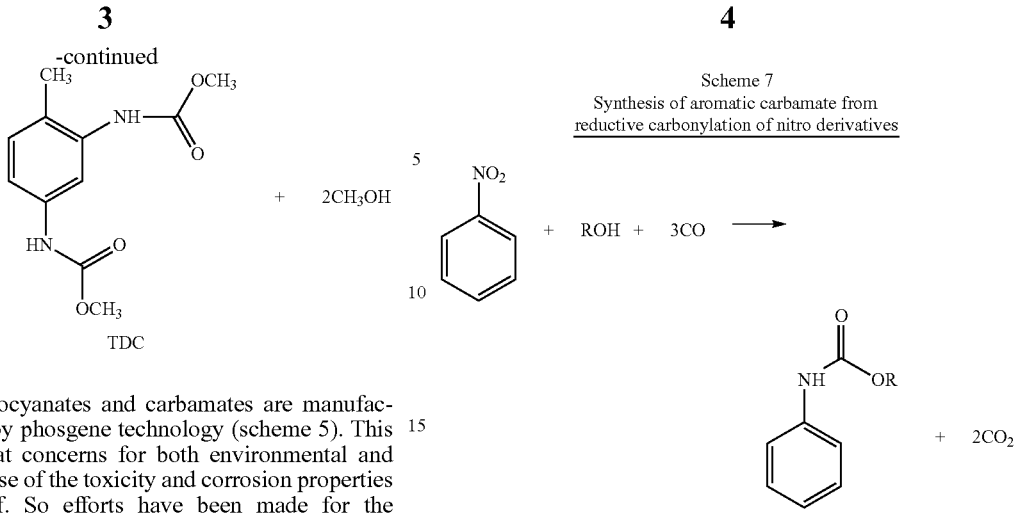

TDC

Presently the Isocyanates and carbamates are manufactured exclusively by phosgene technology (scheme 5). This method poses great concerns for both environmental and safety issues because of the toxicity and corrosion properties of phosgene itself. So efforts have been made for the preparation of isocyanates and carbamates using non-phosgene reagents.

Currently, the studies on phosgene-free synthesis of aromatic carbamates (MPC, MDC and TDU) are mainly focused on oxidative carbonylation of aromatic amines (scheme 6), reductive carbonylation of nitro derivatives (scheme 7), and methoxycarbonylation of amines using DMC as a reagent (scheme 2). The oxidative carbonylation process, suffers from explosion hazards associated with the use of $CO/O_2$ mixture. While in the reductive carbonylation reaction, only one-third of CO could be used efficiently, and the separation of CO from $CO_2$ would increase the operation cost. Additionally, the presence of co-catalysts gives rise to the corrosion problems and makes recovery of the catalyst difficult.

Scheme 5
Synthesis of aromatic carbamate from Phosgen and aniline

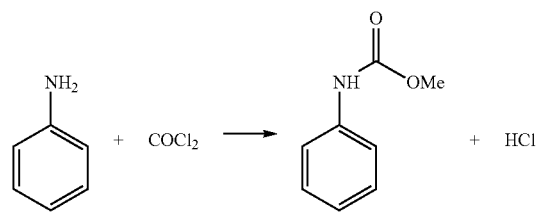

Scheme 6
Synthesis of aromatic carbamate from oxidative carbonylation of aniline

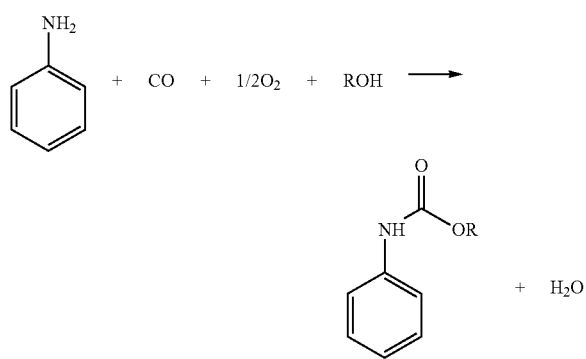

Scheme 7
Synthesis of aromatic carbamate from
reductive carbonylation of nitro derivatives Recently carbamate synthesis by methoxycarbonylation of aromatic amines using DMC as a greener reagent has emerged as promising alternative route. In this reaction methanol is formed as the byproduct, which can be converted back to DMC by oxidative carbonylation of methanol with CO. Thus, the route based on DMC has a potential to provide atom efficient and safer route for the synthesis of carbamates from DMC and amines. Lot of work is being carried out on the development of catalysts for this reaction.

U.S. Pat. No. 8,735,621B2 discloses a process for preparing a carbamate, comprising a reaction between: an amine or a polyamine, an organic carbonate of formula (OR)(OR')C=O, wherein R and R' are independently selected from alkyl group having 1 to 20 carbon atoms, a substituted aryl group, or a non-substituted aryl group, and a catalyst comprising a metal selected from group 8, 9, 10 or 11 of the periodical system placed onto cerium oxide, wherein the particle size of the catalyst is between 1 and 50 nm. In this patent $CeO_2$ is used as support and gold is used as active catalyst component and percentage of gold used is in a range of 0.1-6%. It is mentioned that the catalyst did not lose activity in the recycle experiment. However, detailed recycle study has not been carried out in the patent. Major disadvantage of this invention is the requirement of the catalyst in high quantity. Thus for the reaction of 100 mg of toluenediamine 180 mg of catalyst was used to achieve high yield of the carbamate derivative.

Article titled "Heterogeneous synthesis of dimethylhexane-1,6-dicarbamate from 1,6-hexanediamine and methyl carbonate in methanol over a $CeO_2$ catalyst" by Y Cao et al. published in *Chinese Journal of Chemical Engineering;* 2015; 23 (2), pp 446-450 reports efficient synthesis of dimethylhexane-1,6-dicarbamate (HDC) from 1,6-hexanediamine (HDA) and methyl carbonate over a series of heterogeneous catalysts (e.g., MgO, $Fe_2O_3$, $Mo_2O_3$, and $CeO_2$). The reaction pathway was confirmed as an alcoholysis reaction through a series of designed experiments. Under optimized conditions, 100% HDA conversion with 83.1% $HDC_{total}$ and 16.9% polyurea was obtained using a one-step with high temperature procedure with $CeO_2$ as the catalyst. A new two-step with variable temperature technology was developed based on the reaction pathway to reduce the polyurea yield. Using the proposed method, the $HDC_{total}$ yield reached 95.2%, whereas the polyurea yield decreased to 4.8%. The $CeO_2$ catalyst showed high stability and did not exhibit any observable decrease in the HDC yield or any structural changes after four recycling periods. This paper describes the synthesis of aliphatic dicarbamate (dimethyl-hexane-1,6-dicarbamate) from aliphatic dimine and methyl carbamate as the reactant. This work does not utilize DMC as the reactant and also deals with methoxycarbonylation of aliphatic amines. Also one of the drawback of the present study is low selectivity to dicarbamate product, mainly because of the formation of urea as the by-product in significant quantity (16.9%).

Article titled "Catalytic synthesis of 1,6-dicarbamate hexane over MgO/ZrO$_2$" by F Li et al. published in *J Chem Technol Biotechnol*; 2007, 82; pp 209-213 reports the synthesis of 1,6-dicarbamate hexane (HDC) using dimethyl carbonate (DMC) and 1,6-diamine hexane (HDA) in presence of MgO/ZrO$_2$ catalyst. When the catalyst is calcined at 600° C. and MgO load is 6 wt %, the catalyst exhibits better activity. When the concentration of catalyst is 2 g (100 mL)$^{-1}$ DMC, n(HDA):n(DMC)=1:10, reaction time is 6 h under reflux temperature, and the yield of 1,6-dicarbamate hexane is 53.1%. HDC yield decreases from 53.1% to 35.3% after MgO/ZrO$_2$ being used for three times. Mg/ZrO$_2$ was used as the catalyst for the synthesis of 1,6-dicarbamate hexane. Under optimized reaction conditions (Temperature: 90° C., n(HAD):DMC mole ratio: 1:10, reaction time: 6 h) HDC yield of 53.1, which decreased during recycle study. Major problem of this work is low yield of dicarbamate and decrease in activity during recycle study.

Article titled "Catalytic methoxycarbonylation of aromatic diamines with dimethyl carbonate to their dicarbamates using zinc acetate" by T Baba et al. published in *Catalysis Letters*; 2002, 82 (3-4), pp 193-197 reports methoxycarbonylation of 2,4-toluene diamine and 4,4'-diphenylmethane diamine with dimethyl carbonate to the corresponding dicarbamates using zinc acetate was carried out at 453 K. Zn(OAc)$_2$, prepared by evacuating Zn (OAc)$_2$.2H$_2$O at 383 K for 2 h, yields dimethyltoluene-2,4-dicarbamate in 96% yield in 2 h, while Zn(OAc)$_2$.2H$_2$O yields dimethyl-4,4'-methylenediphenyldicarbamate in 98% yield at 453 K in 2 h. However, the catalyst is homogeneous in nature and separation and recycle of the catalyst is major problem with this work.

Article titled "Synthesis of methyl N-phenyl carbamate from aniline and dimethyl carbonate over supported zirconia catalyst" by F Li et al. published in *Ind. Eng. Chem. Res.*, 2006, 45 (14), pp 4892-4897 reports novel supported zirconia catalysts for the synthesis of methyl N-phenyl carbamate (MPC) from aniline and dimethyl carbonate (DMC). The results show that the synthesis of N-methylaniline (NMA) and DMA are the main competitive reactions to MPC synthesis. The optimal reaction conditions over ZrO$_2$/SiO$_2$ are as follows: reaction temperature, 443.15 K; reaction time, 7 h; n(DMC)/n(aniline)=20; catalyst/aniline=25 wt %; the conversion of aniline is 98.6%; and the yield of MPC is 79.8%. However activity decreased during recycle because of decrease in specific area of the ZrO$_2$/SiO$_2$ catalyst. Thus lower selectivity to MPC and deactivation during recycle are major drawbacks of this work.

Among all metal based catalysts for the synthesis of carbamates from DMC, Zn and Pb metal salts have shown best catalytic activity. However, catalyst/product separation is difficult because of the homogeneous nature of these catalysts. Also, lead compounds showed high catalytic performance, but they are not environmentally friendly. Supported zinc acetate based catalysts were studied for this reaction, namely (Zn(OAc)$_2$/AC, Zn(OAc)$_2$/α-Al$_2$O$_3$ and Zn(OAc)$_2$/SiO$_2$, however, deactivation of Zn(OAc)$_2$ was observed with the formation of ZnO [reaction between methanol and Zn(OAc)$_2$] (Wang et. al). [Applied Catalysis A: General 475 (2014) 355-362].

There are several patents as well as publications in recent times on the synthesis of MPC from aniline and DMC leading to the development of new and improved catalysts and methodologies for this important reaction. However, recycle of the catalyst is one of the issues with reported catalysts. Therefore, there is need for an efficient and environment friendly process for the synthesis of aromatic carbamates with easy recycle of catalyst used.

BRIEF SUMMARY

The main objective of the present invention is to provide a process for the synthesis of aromatic carbamates with high selectivity and conversion.

Accordingly, the present invention provides a process for the synthesis of aromatic carbamates comprises reacting amine with dialkyl carbonate in the presence of the binary or ternary mixed metal oxide catalyst at a temperature in the range of 100 to 220° C. for a period in the range of 1 to 15 hrs to obtain corresponding aromatic carbamate.

In one embodiment of the present invention, the process for the synthesis of aromatic carbamates is optionally carried out in presence of solvent.

In preferred embodiment, the solvent is selected from methanol or ethanol.

In an embodiment, the amine is selected from aromatic amine or substituted aromatic amine.

Preferably, the amine is selected from compound of formula (I);

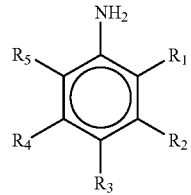

Formula (I)

Wherein R$_1$, R$_2$, R$_3$, R$_4$ and R$_5$ are same or different and are selected from hydrogen, alkyl, alkoxy, —NH$_2$, halide, —NO$_2$,

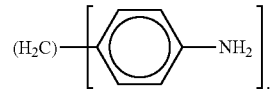

In more preferred embodiment, the amine is selected from aniline, 4-methylbenzene-1,3-diamine, 4,4'-methylenedianiline, 2,4-dimethylaniline, 3,4-dimethylaniline, 2,6-dimethylaniline, 4-chloroaniline, 4-methoxyaniline, o-toluidine, m-toluidine, p-toluidine, 2,4-diamino toluene, 4,4-Diaminodiphenyl methane, toluene diamine or diamino diphenyl methane.

The dialkyl carbonate is selected from dimethyl carbonate or diethyl carbonate.

In one embodiment, the binary or ternary mixed metal catalyst for the synthesis of aromatic carbamates is X$_a$Y$_b$Z$_c$O$_d$, wherein X is at least one metal selected from Group 3 elements, Y is at least one metal selected from transition metals of the Periodic Table, Z is at least one of the metal/metalloid selected from zirconium, aluminium and silica; a, b and c are the molar ratios of their respective components, a, b and c can vary from 0 to 3 respectively, and d is the number of oxygen atoms (O) necessary to satisfy the valence of the other components.

In preferred embodiment, the binary or ternary mixed metal catalyst is selected from Ce:Zr, Zn:Zr, Y:Zr, Ce:Al, Zr:Y, Zn:Y, Zn:Al, Ni:Al, Co:Al, Ce:Fe, Zn:Fe, Ce:Zn:Zr, Zn:Zr:Y, Y:Zn:Zr or La:Mg:Al.

The ratio of amine to dialkyl carbonate is in the range of 1:2 to 1:30.

The concentration of catalyst is in the range of 1 to 20 weight % of the amine.

The yield of the aromatic carbamate is in the range of 20 to 99% and preferably in the range of 60-99%.

The aromatic carbamate is selected from N-methyl phenyl carbamate (MPC), dimethyl toluene-2,4,dicarbamate (TDC), methylene diphenyl-4,4'-dicarbamate (MDC), methyl (2,6-dimethylphenyl)carbamate, methyl (4-chlorophenyl)carbamate, methyl (4-methoxyphenyl)carbamate, methyl o-tolylcarbamate or methyl m-tolylcarbamate.

Abbreviations Used

TDC: dimethyl toluene-2,4,dicarbamate
MDC: methylene diphenyl-4,4'-dicarbamate
DADPM: 4,4'-Diaminodiphenylmethane
TDA: toluene diamine
DMC: Dimethyl carbonate
MPC: Methyl N-phenyl carbamate
MMPC: Methyl N-methylphenyl carbamate
NMA: N-methyl aniline
NNDMA: N,N-dimethyl aniline

DETAILED DESCRIPTION OF VARIOUS EMBODIMENTS

Figure 1:
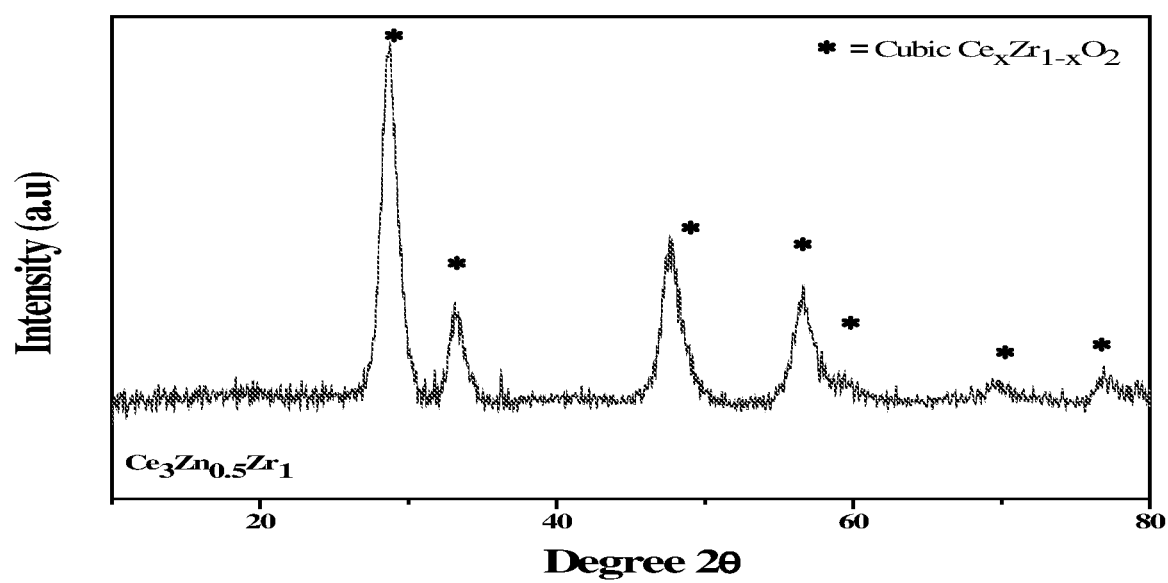
FIG. 1: XRD patterns of $Ce_3Zn_{0.5}Zr_1$ catalyst.

The present invention will now be described in preferred as well as optional embodiments so that the various aspects disclosed therein will be more clearly understood and appreciated.

In view of the above, the present invention provides a process for the synthesis of aromatic carbamate from amine and dialkyl carbonate in the presence of the mixed metal oxide catalyst of formula $X_aY_bZ_cO_d$, wherein X is at least one metal selected from Group 3 elements, Y is at least one metal selected from transition metals of the Periodic Table, Z is at least one of the metal/metalloid selected from zirconium, aluminium and silica; a, b and c are the molar ratios of their respective components, a, b and c can vary from 0 to 3 respectively, and d is the number of oxygen atoms (O) necessary to satisfy the valence of the other components.

In an embodiment, the present invention provides a process for the synthesis of aromatic carbamate comprises reacting amine with dialkyl carbonate in the presence of the binary or ternary mixed metal oxide catalyst at a temperature in the range of 100 to 220° C. for a period in the range of 1 to 15 hrs to obtain corresponding aromatic carbamate.

In one embodiment of the present invention, the process for the synthesis of aromatic carbamates is optionally carried out in presence of solvent.

In preferred embodiment, the solvent is selected from methanol or ethanol.

In another embodiment, the amine is selected from aromatic amine or substituted aromatic amine. Preferably, the amine is selected from compound of formula (I);

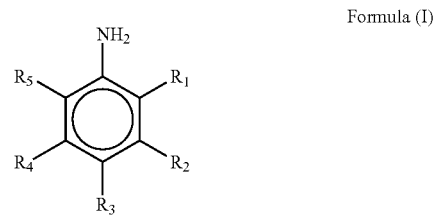

Formula (I)

Wherein $R_1$, $R_2$, R3, $R_4$ and $R_5$ are same or different and are selected from hydrogen, alkyl, alkoxy, $-NH_2$, halide, $-NO_2$,

,

In more preferred embodiment, the amine is selected from aniline, 4-methylbenzene-1,3-diamine, 4,4'-methylenedianiline, 2,4-dimethylaniline, 3,4-dimethylaniline, 2,6-dimethylaniline, 4-chloroaniline, 4-methoxyaniline, o-toluidine, m-toluidine, p-toluidine, toluene diamine or diamine diphenyl methane, toluenediamine or diamonidiphenyl methane.

The dialkyl carbonate is selected from dimethyl carbonate or diethyl carbonate.

Ternary or binary metal oxides, $(X_aY_bZ_cO_d)$ are used as catalysts for the synthesis of aromatic carbamates. X is at least one metal selected from Group 3 elements (including the Lanthanides and Actinides) i.e X is selected from cerium, samarium, lanthanum, yttrium, dysprosium, erbium, europium, gadolinium, holmium, lutetium, neodymium, praseodymium, promethium, scandium, terbium, thulium and ytterbium. And Y is at least one metal selected from transition metals of the Periodic Table, i.e zinc, cobalt, iron, manganese, nickel, tungsten or copper and Group 2 of the Periodic Table of Elements, such as magnesium, calcium, strontium or barium. Where Z is at least one of the metal/metalloid selected from zirconium, aluminium and silica; a, b and c are the molar ratios of their respective components, a, b and c can vary from 0 to 3 respectively, and d is the number of oxygen atoms (O) necessary to satisfy the valence of the other components.

The ternary/binary mixed metal oxides are synthesized by co-precipitation method followed by calcination at different temperatures in a range of 450 to 850° C. In a preferred embodiment, the synthesis of the ternary CeZnZr mixed metal oxide by co-precipitation method is disclosed. The molar ratio of Ce/Zr is 3:1 and concentration of Zn varied between 0-2.

CeZnZr mixed metal oxide is an efficient, stable, inexpensive and recyclable, heterogeneous catalyst. This catalyst is not dissociated under reaction conditions employed for the synthesis of carbamates.

In preferred embodiment, the binary or ternary mixed metal catalyst is selected from Ce:Zr, Zn:Zr, Y:Zr, Ce:Al, Zr:Y, Zn:Y, Zn:Al, Ni:Al, Co:Al, Ce:Fe, Zn:Fe, CeZnZr, Zn:Zr:Y, Y:Zn:Zr or La:Mg:Al.

The ratio of amine to dialkyl carbonate is in the range of 1:20 to 1:30 and the concentration of catalyst is in the range of 1-20 weight % of the amine.

The yield of the aromatic carbamate is in the range of 20 to 99% and preferably in a range of 60 to 99%.

The aromatic carbamate is selected from N-methyl phenyl carbamate (MPC), dimethyl toluene-2,4,dicarbamate (TDC), methylene diphenyl-4,4'-dicarbamate (MDC), methyl (2,4-dimethylphenyl)carbamate, methyl (3,4-dimethylphenyl)carbamate, methyl (2,6-dimethylphenyl)carbamate, methyl (4-chlorophenyl)carbamate, methyl (4-methoxyphenyl)carbamate, methyl o-tolylcarbamate or methyl m-tolylcarbamate.

In a preferred embodiment, aromatic amines are reacted with DMC (aromatic amine:DMC mole ratio of 1:20), at catalyst concentration of 10 wt % relative to amine, for 2 h at 180° C. to obtain the corresponding aromatic N-methyl carbamates.

As shown in Table 2, aromatic amines screened are all compatible with this catalyst, leading to the corresponding N-methyl carbamates with good selectivity.

The process is carried out at 100 to 220° C. temperature with stirring speed in the range of 900 to –1200 rpm.

In another preferred embodiment, the present invention discloses synthesis of N-methyl phenyl carbamate from aniline and dimethyl carbonate using CeZnZr mixed metal oxide as a catalyst. The selectivity obtained towards MPC is greater than 90%.

The XRD pattern of $Ce_3Zn_{0.5}Zr_1$ mixed metal oxide (MMO) catalyst is shown in FIG. 1. The peaks that appear at 28.8°, 33.4°, 48°, 57° and 59.8° are the typical diffractions of $Ce_xZr_{1-x}O_2$ material (PCPDF-28-0271). And the peaks related to ZnO appearing at 31.7°, 34.4°, 36.2°, 47.4°, 56.5°, 68.9° and 67.8° (PCPDF-80-0075) was not observed indicating fine dispersion of ZnO on CeZr surface. XRD pattern of $Ce_3Zn_{0.5}Zr_1$ material indicates the formation of crystalline structure with cubic symmetry.

Figure 2:
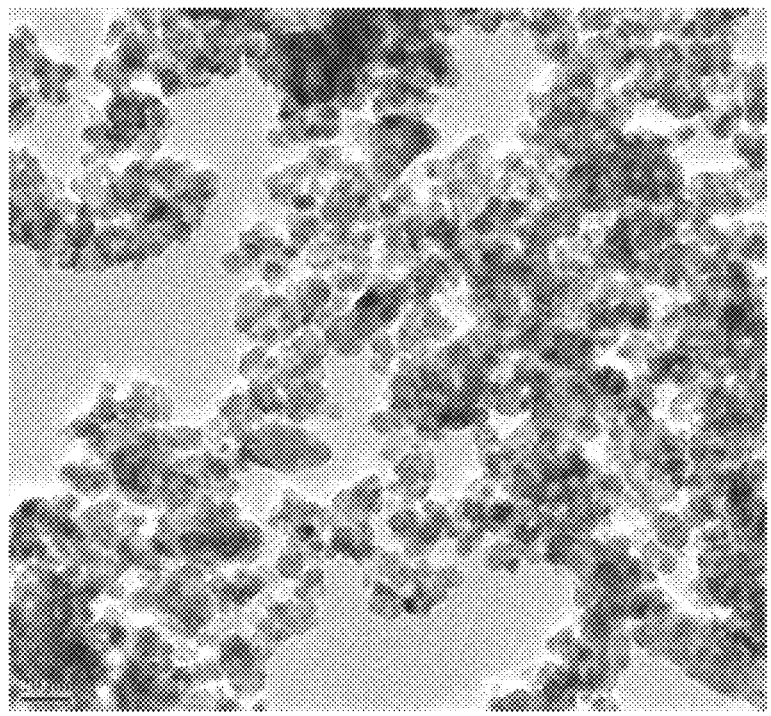
FIG. 2: (A) TEM image of $Ce_3Zn_{0.5}Zr_1$ (B) SAED image of $Ce_3Zn_{0.5}Zr_1$
Figure 2:

To check the morphology and crystalline nature of the catalyst, TEM and SAED images of the catalyst is taken on carbon coated grid (FIGS. 2A and B). From FIG. 2A homogeneous distributions of small sized particles of ~6-20 nm are observed. Poly crystalline nature of the synthesized material was observed from SAED image (FIG. 2B). The crystalline phases are in good agreement with the XRD pattern.

Further the reaction may be applied for the synthesis of MDC (methylenediphenyl dicarbamate) and TDC (Toluene dicarbamate) which are used in polyurethane foams.

EXAMPLES

Following examples are given by way of illustration and therefore should not be construed to limit the scope of the invention.

Example 1: General Process for Catalyst Preparation

Binary/Ternary mixed metal oxides were synthesized by co-precipitation method. The solution A contains binary or ternary mixture of metal precursors in appropriate molar ratios dissolved in distilled water. Solution B contains NaOH (1.2 M) and $Na_2CO_3$ (0.1 M) dissolved in distilled water. The solutions A and B were simultaneously added drop wise in 100 ml de-ionized water with vigorous stirring at 30° C. During addition, pH of the solution was maintained at 10-11 by addition of appropriate amount of solution B. The formed suspension was continuously stirred for 30 min and aged at 70° C. for 12 h. Finally the solid formed was separated by filtration and washed thoroughly with de-ionized water until pH of the water wash became neutral. Resultant solid was then dried at 100° C. for 12 h. The obtained solid power was calcined at 450-850° C. for 6 hours in air.

Example 2: Process for Preparation of $Ce_3Zn_{0.5}Zr_1$

Ternary $Ce_3Zn_{0.5}Zr_1$ mixed metal oxides was synthesized by co-precipitation method. The solution A contains ternary mixture of metal precursors i.e $Ce(NO_3)_3.6H_2O$ [30 mmol], $Zn(NO_3).6H_2O$ [0.5 mmol], $ZrO(NO_3)_2.xH_2O$ [10 mmol] dissolved in distilled water. Solution B contains NaOH (1.2 M) and $Na_2CO_3$ (0.1 M) dissolved in distilled water. The solutions A and B were simultaneously added drop wise in 100 ml de-ionized water with vigorous stirring at room temperature. During addition, pH of the solution was maintained at 10-11 by addition of appropriate amount of solution B. The formed suspension was continuously stirred for 30 min and aged at 70° C. for 12 h. Finally the solid formed was separated by filtration and washed thoroughly with deionized water until pH of the water wash became neutral. Resultant solid was then dried at 100° C. for 12 h. The obtained solid power was calcined at 550° C. for 6 hours in air.

Characterization of $Ce_3Zn_{0.5}Zr_1$:

XRD:

The XRD pattern of $Ce_3Zn_{0.5}Zr_1$ mixed metal oxide (MMO) catalyst is shown in FIG. 1. The peaks that appear at 28.8°, 33.4°, 48°, 57° and 59.8° are the typical diffractions of $Ce_xZr_{1-x}O_2$ material (PCPDF-28-0271). And the peaks related to ZnO appearing at 31.7°, 34.4°, 36.2°, 47.4°, 56.5°, 68.9° and 67.8° (PCPDF-80-0075) was not observed indicating fine dispersion of ZnO on CeZr surface. XRD pattern of $Ce_3Zn_{0.5}Zr_1$ material indicates the formation of crystalline structure with cubic symmetry.

TEM: To check the morphology and crystalline nature of the catalyst, TEM and SAED images of the catalyst was taken on carbon coated grid (FIGS. 2A and B).

From FIG. 2A homogeneous distributions of small sized particles of ~6-20 nm were observed. Poly crystalline nature of the synthesized material was observed from SAED image (FIG. 2B). The crystalline phases are in good agreement with the XRD pattern.

Example 3:—Synthesis of Aromatic Carbamate (MPC)

The reaction of aniline and DMC was carried out in a 50 mL stainless autoclave (Parr reactor) with constant stirring. In a typical experiment aniline 16.64 mmol (1.55 gm), DMC 333 mmol (30 gm) and $Ce_3Zn_{0.5}Zr_1$ mixed metal oxide catalyst 0.155 gm (10 wt % relative to aniline), were charged to the reactor. The reactor was heated to 180° C. with slow stirring. The reaction was initiated by stirring the reactor at 900 rpm for desired time of 2 h. The reactor was cooled to 30° C., the catalyst was recovered by centrifugation, and the quantitative analysis of the reaction mixture was carried out using Agilent 6890 GC (FTD detector, Innowax column).

TABLE 1

Synthesis of MPC from aniline and DMC using
different binary and ternary mixed metal oxides

| Sr.no. | Catalyst | Conversion Aniline (%) | Selectivity MPC (%) |
|---|---|---|---|
| 1 | Ce:Zr (3:1) | 50 | 56 |
| 2 | Zn:Zr (3:1) | 53 | 40 |
| 3 | Y:Zr (3:1) | 41.58 | 52 |
| 4 | Ce:Al (3:1) | 33 | 60 |
| 5 | Zr:Y (3:1) | 30.5 | 42 |
| 6 | Zn:Y (3:1) | 23.4 | 46 |
| 7 | Zn:Al (3:1) | 20.5 | 34.2 |
| 8 | Ni:Al (3:1) | 19.8 | 12.5 |
| 9 | Co:Al (3:1) | 26.3 | 58 |
| 10 | Ce:Fe (3:1) | 29.94 | 62 |
| 11 | Zn:Fe (3:1) | 31.58 | 42 |
| 12 | Ce:Zn:Zr (3:0.5:1) | 98.4 | 98.8 |
| 13 | Zn:Zr:Y (3:0.5:1) | 49 | 68 |
| 14 | Y:Zn:Zr (3:0.5:1) | 64 | 78 |
| 15 | La:Mg:Al (3:0.5:1) | 45 | 62 |

Reaction conditions:
aniline: 1.55 gm,
DMC: 30 gm,
Catalyst: 10 wt % relative to aniline,
Reaction Time: 2 h, Temperature: 180° C.

Example 4:—Synthesis of Aromatic Carbamates Using $Ce_3Zn_{0.5}Zr_1$ as the Catalyst A set of aromatic amines were reacted with DMC under the optimized reaction conditions and the results of these experiments are presented in Table 2.

TABLE 2

$Ce_3Zn_{0.5}Zr_1$ catalyzed synthesis of
aromatic N-methyl carbamates

| Entry | Aromatic amine | Conversion (%) | Selectivity (%) |
|---|---|---|---|
| 1 | O-Toluidine | 82.5 | 94.2 |
| 2 | m-Toluidine | 86.8 | 95 |
| 3 | p-Toluidine | 89 | 95.7 |

Reaction conditions:
Amine: 16.44 mmol,
Amine: DMC = 1:20,
Catalyst: 10 wt % relative to amine,
Reaction Time: 2 h, Temperature: 180° C.

Example 5: Experimental Procedure for Recycle of CeZnZr Ternary Mixed Metal Oxide Reaction of aniline and DMC was carried out as per the procedure described earlier. The catalyst from the reaction mixture was recovered by centrifugation, washed with DMC, and then dried overnight at 373 K for 12 h and calcined at 550° C./6 hin air. The recovered catalyst was used to perform a new reaction by charging aniline and DMC to the reactor. Catalyst was recycled two times using the same procedure and the results are presented in Table 3.

TABLE 3

Recycle study using CeZnZr ternary
mixed metal oxide catalyst

| | Aniline Conversion (%) | MPC Selectivity (%) |
|---|---|---|
| Fresh | 98.4 | 98.8 |
| Recycle 1 | 97.5 | 97.4 |
| Recycle 2 | 94.1 | 97.2 |
| Recycle 3 | 92 | 97.5 |
| Recycle 4 | 91.4 | 96.6 |
| Recycle 5 | 90.5 | 96 |

Reaction conditions:
Amine: 16.44 mmol,
Amine: DMC = 1:20,
Catalyst: 10 wt % relative to amine,
Reaction Time: 2 h, Temperature: 180° C.

Example 6: Synthesis of TDC

Reaction of TDA to TDC was carried out as per the procedure described earlier in example 3. In this reaction TDA was used instead of aniline. The results are tabulated in table 4.

TABLE 4

Methoxycarbonylation of TDA to TDC

| Entry | Aromatic amine | Conversion (%) | Selectivity of TDC (%) |
|---|---|---|---|
| 1 | TDA | 96.8 | 18.6 |
| 2* | TDA | 79.2 | 5.7 |

Reaction conditions:
TDA: 8.18 mmol,
Amine: DMC = 1:30,
Catalyst ($Ce_3Zn_{0.5}Zr_1$): 30 wt % relative to TDA, Methanol (solvent) = 81.8 mmol,
Reaction Time: 2 h, Temperature: 180° C.
*Reaction conditions:
TDA: 12.27 mmol,
Amine: DMC = 1:30,
Catalyst ($Ce_3Zn_{0.5}Zr_1$): 10 wt % relative to TDA,
Reaction Time: 2.5 h, Temperature: 190° C. In this reaction methanol was not used as solvent

Example 7: Synthesis of MDC

Reaction of DADPM to MDC was carried out as per the procedure described earlier in example 3. In this reaction DADPM was used instead of aniline. The results are tabulated in table 5.

TABLE 5

Methoxycarbonylation of DADPM to MDC

| Entry | Aromatic amine | Conversion (%) | Selectivity of MDC (%) |
|---|---|---|---|
| 1 | DADPM | 86.7 | 33.3 |

Reaction conditions:
DADPM: 10.08 mmol,
Amine: DMC = 1:30,
Catalyst ($Ce_3Zn_{0.5}Zr_1$): 30 wt % relative to DADPM, Methanol (solvent) = 100 mmol,
Reaction Time: 3 h, Temperature: 180° C.

Example 8: Methoxycarbonylation of Aniline with $Ce_3Zn_{0.5}Zr_1$ Catalyst

Reaction of aniline and DMC was carried out as per the procedure described earlier in example 3. The effect of various reaction parameters on the reaction conversion and selectivity such as effect of catalyst loading, effect of aniline:DMC molar ratio, effect of temperature is tabulated in table 6, 7 and 8 respectively.

TABLE 6

Effect of catalyst loading

| Entry | Catalyst loading (wt %) | Time (h) | Aniline conversion (%) | Selectivity (%) | | | |
|---|---|---|---|---|---|---|---|
| | | | | MPC | MMPC | NMA | NNDMA |
| 1 | 0 | 2 | 0 | NA | NA | NA | NA |
| 2 | 5 | 2 | 87 | 95.8 | 1 | 2.3 | 0.39 |
| 3 | 10 | 2 | 98.4 | 98.6 | 0.1 | 1.2 | 0.09 |
| 4 | 15 | 2 | 96.3 | 96.6 | 1.6 | 1.5 | 0.2 |

Reaction conditions: Aniline: 1.55 gm, DMC: 30 gm, Aniline/DMC: 1/20, Catalyst ($Ce_3Zn_{0.5}Zr_1$): 5-15 wt % relative to aniline, Reaction Time: 2 h, Temperature: 180° C.

TABLE 7

Effect of aniline:DMC molar ratio

| Entry | Molar ratio Aniline:DMC | Time (h) | Aniline conversion (%) | Selectivity (%) | | | |
|---|---|---|---|---|---|---|---|
| | | | | MPC sel. | MMPC | NMA | NNDMA |
| 1 | 1:5 | 2 | 96.6 | 87 | 2.6 | 7 | 3.2 |
| 2 | 1:10 | 2 | 89 | 93.2 | 0.67 | 3.4 | 0.8 |
| 3 | 1:20 | 2 | 98.4 | 98.6 | 0.1 | 1.2 | 0.09 |

Reaction conditions: Aniline:DMC molar ratio = 1:5 to 1:20, Catalyst ($Ce_3Zn_{0.5}Zr_1$): 10 wt %, Reaction Time: 2 h, Temperature: 180° C.

TABLE 8

Effect of Temperature

| Entry | Reaction temperature | Time (h) | Aniline conv. (%) | Selectivity (%) | | | |
|---|---|---|---|---|---|---|---|
| | | | | MPC | MMPC | NMA | NNDMA |
| 1 | 170 | 2 | 80.5 | 97 | 0.6 | 2.2 | 0.2 |
| 2 | 180 | 2 | 98.4 | 98.6 | 0.1 | 1.2 | 0.09 |
| 3 | 190 | 2 | 97.5 | 96 | 1.6 | 1.9 | 1 |

Reaction conditions: Aniline: 1.55 gm, DMC: 30 gm, Aniline/DMC: 1/20, Catalyst ($Ce_3Zn_{0.5}Zr_1$): 10 wt % relative to aniline, Reaction Time: 2 h, Temperature: 170-190° C.

ADVANTAGES OF THE INVENTION

Recyclability of the catalyst
No leaching of catalyst during recovery process
High conversion of starting materials

We claim:

1. A process for the synthesis of aromatic carbamate, the process comprising the step of reacting amine with dialkyl carbonate in the presence of a binary or ternary mixed metal oxide catalyst at a temperature in the range of 100 to 220° C. and for a period in the range of 1 to 15 hours to obtain corresponding aromatic carbamate, wherein yield of said aromatic carbamate is in the range of 60 to 99%.

2. The process as claimed in claim 1, wherein said process is carried out in presence of solvent.

3. The process as claimed in claim 1, wherein said amine is selected from compound of formula (I);

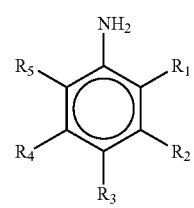

Formula (I)

wherein $R_1$, $R_2$, $R_3$, $R_4$ and $R_5$ are same or different and are selected from hydrogen, alkyl, alkoxy, —$NH_2$, halide, —$NO_2$,

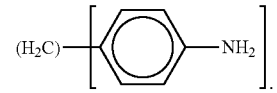

4. The process as claimed in claim 3, wherein said amine is selected from aniline, 4-methylbenzene-1,3-diamine, 4,4'-methylenedianiline, 2,4-dimethylaniline, 3,4-dimethylaniline, 2,6-dimethylaniline, 4-chloroaniline, 4-methoxyaniline, o-toluidine, m-toluidine, p-toluidine, toluene diamine or diaminodiphenyl methane.

5. The process as claimed in claim 1, wherein said dialkyl carbonate is selected from dimethyl carbonate or diethyl carbonate.

6. The process as claimed in claim 1, wherein said binary or ternary mixed metal oxide catalyst is $X_aY_bZ_cO_d$, wherein X is at least one metal selected from Group 3 elements, Y is at least one metal selected from transition metals of the Periodic Table, Z is at least one of the metal/metalloid selected from zirconium, aluminium and silica; a, b and c are the molar ratios of their respective components, a, b and c can vary from 0 to 3 respectively, and d is the number of oxygen atoms (O) necessary to satisfy the valence of the other components.

7. The process as claimed in claim 6, wherein said binary or ternary mixed metal oxide catalyst is selected from Ce:Zr (3:1), Zn:Zr (3:1), Y:Zr (3:1), Ce:Al (3:1), Zr:Y (3:1), Zn:Y (3:1), Zn:Al (3:1), Ni:Al (3:1), Co:Al (3:1), Ce:Fe (3:1), Zn:Fe (3:1), CeZnZr (3:0.5:1), Zn:Zr:Y (3:0.5:1), Y:Zn:Zr (3:0.5:1), or La:Mg:Al (3:0.5:1).

8. The process as claimed in claim 7, wherein said catalyst is the ternary mixed metal oxide $Ce_3Zn_{0.5}Zr_1$.

9. The process as claimed in claim 1, wherein the ratio of amine to dialkyl carbonate is in the range of 1:2 to 1:30.

10. The process as claimed in claim 1, wherein said aromatic carbamate is selected from N-methyl phenyl carbamate (MPC), dimethyl toluene-2,4,dicarbamate (TDC), methylene diphenyl-4,4'-dicarbamate (MDC), methyl (2,4-dimethylphenyl)carbamate, methyl (3,4-dimethylphenyl) carbamate, methyl (2,6-dimethylphenyl)carbamate, methyl (4-chlorophenyl)carbamate, methyl (4-methoxyphenyl)carbamate, methyl o-tolylcarbamate, methyl m-tolylcarbamate.

* * * * *